United States Patent
Hwang

(10) Patent No.: US 7,618,956 B2
(45) Date of Patent: Nov. 17, 2009

(54) REDUCTION OF HAIR GROWTH

(75) Inventor: Cheng Shine Hwang, Framingham, MA (US)

(73) Assignee: The Gillette Company, Boston, MA (US)

(*) Notice: Subject to any disclaimer, the term of this patent is extended or adjusted under 35 U.S.C. 154(b) by 535 days.

(21) Appl. No.: 11/141,798

(22) Filed: May 31, 2005

(65) Prior Publication Data

US 2006/0269496 A1 Nov. 30, 2006

(51) Int. Cl.
- *A61K 31/56* (2006.01)
- *A61K 31/59* (2006.01)
- *A61K 31/20* (2006.01)
- *A61K 8/19* (2006.01)
- *A61K 8/18* (2006.01)

(52) U.S. Cl. ............... 514/182; 514/169; 514/171; 514/559; 424/70.1; 424/73

(58) Field of Classification Search ............... 424/70.1, 424/73; 514/169, 171, 182
See application file for complete search history.

(56) References Cited

U.S. PATENT DOCUMENTS

| | | |
|---|---|---|
| 3,426,137 A | 2/1969 | Philpitt et al. |
| 3,878,239 A | 4/1975 | Hyashi et al. |
| 4,039,669 A | 8/1977 | Beyler et al. |
| 4,139,638 A | 2/1979 | Neri et al. |
| 4,161,540 A | 7/1979 | Neri et al. |
| 4,185,099 A | 1/1980 | Sorbini |
| 4,191,775 A | 3/1980 | Glen |
| 4,201,873 A | 5/1980 | Peterson |
| 4,203,924 A | 5/1980 | Nelson |
| 4,269,831 A | 5/1981 | Ferrari et al. |
| 4,370,315 A | 1/1983 | Greff et al. |
| 4,508,714 A | 4/1985 | Cecic et al. |
| 4,517,175 A | 5/1985 | Iwabuchi et al. |
| 4,562,204 A | 12/1985 | Wakatsuka et al. |
| 4,720,489 A | 1/1988 | Shander |
| 4,885,289 A | 12/1989 | Breuer et al. |
| 4,935,231 A | 6/1990 | Pigiet |
| 5,095,007 A | 3/1992 | Ahluwalia |
| 5,096,911 A | 3/1992 | Ahluwalia et al. |
| 5,132,293 A | 7/1992 | Shander et al. |
| 5,143,925 A | 9/1992 | Shander et al. |
| 5,183,817 A | 2/1993 | Bazzano |
| 5,189,212 A | 2/1993 | Ruenitz |
| 5,271,942 A | 12/1993 | Heverhagen |
| 5,300,284 A | 4/1994 | Wiechers et al. |
| 5,328,686 A | 7/1994 | Shander et al. |
| 5,362,748 A | 11/1994 | Schwen et al. |
| 5,364,885 A | 11/1994 | Ahluwalia et al. |
| 5,411,991 A | 5/1995 | Shander et al. |
| 5,444,090 A | 8/1995 | Ahluwalia |
| 5,455,234 A | 10/1995 | Ahluwalia et al. |
| 5,468,476 A | 11/1995 | Ahluwalia et al. |
| 5,474,763 A | 12/1995 | Shander et al. |
| 5,554,608 A | 9/1996 | Ahluwalia et al. |
| 5,645,825 A | 7/1997 | Hillebrand et al. |
| 5,648,394 A | 7/1997 | Boxall et al. |
| 5,652,273 A | 7/1997 | Henry et al. |
| 5,674,477 A | 10/1997 | Ahluwalia |
| 5,700,835 A | 12/1997 | Dean et al. |
| 5,728,736 A | 3/1998 | Shander et al. |
| 5,776,442 A | 7/1998 | Ahluwalia |
| 5,824,665 A | 10/1998 | Henry et al. |
| 5,824,694 A | 10/1998 | Kurtz et al. |
| 5,840,752 A | 11/1998 | Henry et al. |
| 5,866,595 A | 2/1999 | Pershadsingh et al. |
| 5,908,867 A | 6/1999 | Henry et al. |
| 5,939,458 A | 8/1999 | Henry et al. |
| 5,958,946 A | 9/1999 | Styczynski et al. |
| 5,962,466 A | 10/1999 | Styczynski et al. |
| 5,972,944 A | 10/1999 | Antonucci et al. |
| 6,020,006 A | 2/2000 | Styczynski et al. |
| 6,037,326 A | 3/2000 | Styczynski et al. |
| 6,060,471 A | 5/2000 | Styczynski et al. |
| 6,060,515 A | 5/2000 | Elias et al. |
| 6,071,955 A | 6/2000 | Elias et al. |
| 6,093,748 A | 7/2000 | Ahluwalia et al. |
| 6,121,269 A | 9/2000 | Henry et al. |
| 6,187,814 B1 | 2/2001 | Elias et al. |
| 6,218,435 B1 | 4/2001 | Henry et al. |
| 6,235,737 B1 | 5/2001 | Styczynski et al. |
| 6,239,170 B1 | 5/2001 | Ahluwalia et al. |
| 6,248,751 B1 | 6/2001 | Ahluwalia et al. |

(Continued)

FOREIGN PATENT DOCUMENTS

EP 0 532 219 A2 9/1992

(Continued)

OTHER PUBLICATIONS

Claudel et al. "The Farnesoid X Receptor: A Novel Drug Target?" Expert Opin. Investig. Drugs, (2004) 13(9): pp. 1135-1148.*

(Continued)

*Primary Examiner*—Jennifer M Kim
*Assistant Examiner*—Jody L Karol
(74) *Attorney, Agent, or Firm*—Fish & Richardson P.C.

(57) ABSTRACT

Mammalian hair growth is reduced by applying an agonist of farnesoid X receptor.

11 Claims, No Drawings

U.S. PATENT DOCUMENTS

| | | | |
|---|---|---|---|
| 6,284,234 | B1 | 9/2001 | Niemiec et al. |
| 6,299,865 | B1 | 10/2001 | Styczynski et al. |
| 6,369,098 | B1 | 4/2002 | Pershadsingh et al. |
| 6,414,017 | B2 | 7/2002 | Ahluwalia et al. |
| 6,419,913 | B1 | 7/2002 | Niemiec et al. |
| 6,452,032 | B1 | 9/2002 | Beard et al. |
| 6,613,780 | B2 | 9/2003 | Yokota et al. |
| 6,743,419 | B1 | 6/2004 | Shander et al. |
| 6,743,822 | B2 | 6/2004 | Styczynski et al. |
| 2002/0019338 | A1 | 2/2002 | Hebert |
| 2002/0044953 | A1 | 4/2002 | Michelet et al. |
| 2002/0045659 | A1 | 4/2002 | Michelet et al. |
| 2002/0052414 | A1 | 5/2002 | Bernard et al. |
| 2002/0052416 | A1 | 5/2002 | Michelet et al. |
| 2003/0012755 | A1* | 1/2003 | Styczynski et al. ......... 424/70.1 |
| 2003/0187042 | A1 | 10/2003 | Bauer et al. |
| 2004/0176426 | A1 | 9/2004 | Houze et al. |
| 2004/0180942 | A1 | 9/2004 | Martin et al. |
| 2004/0192778 | A1 | 9/2004 | Jardien et al. |

FOREIGN PATENT DOCUMENTS

| | | | |
|---|---|---|---|
| GB | 1 458 349 | | 12/1976 |
| JP | 2005015408 | A * | 1/2005 |
| WO | WO 92/10164 | | 6/1992 |
| WO | WO 94/21216 | | 9/1994 |
| WO | WO 98/02134 | | 1/1998 |
| WO | WO 00/50002 | | 8/2000 |
| WO | WO 01/54654 | A2 | 8/2001 |
| WO | WO 01/62237 | A3 | 8/2001 |
| WO | WO 02/072598 | | 9/2002 |
| WO | WO 03/002756 | A1 | 1/2003 |
| WO | WO 03/015771 | | 2/2003 |
| WO | WO 03/060078 | | 7/2003 |
| WO | WO 03/076418 | | 9/2003 |
| WO | WO 03/080803 | A2 | 10/2003 |
| WO | WO 2004/007521 | | 1/2004 |
| WO | WO 2004/046162 | | 6/2004 |
| WO | WO 2004/048349 | | 6/2004 |

OTHER PUBLICATIONS

Torra et al., "Identification of DRIP205 as a Coactivator for the Farnesoid X Receptor", The Journal of Biology Chemistry, vol. 279, No. 35, pp. 36184-36191, Aug. 27, 2004.

Lew et al., "The Farnesoid X Receptor Controls Gene Expression in a Ligand- and Promoter-Selection Fashion", The Journal of Biological Chemistry, vol. 279, No. 10, pp. 8856-8861, Mar. 5, 2004.

Zhang et al., "Peroxisome Proliferator-Activated Receptor-γ Coactivator 1α (PGC-1α) Regulates Triglyceride Metabolism by Activation of the Nuclear Receptor FXR", Genes & Development 18:157-169, 2004.

Houck et al., "T0901317 is a Dual LXR/FXR Agonist", Molecular Genes and Metabolism, 83, pp. 184-187, 2004.

Pellicciari et al., "Bile Acid Derivatives as Ligands of the Farnesoid X Receptor, Synthesis, Evaluation, and Structure-Activity Relationship of a Series of Body and Side Chain Modified Analogues of Chenodeoxycholic Acid", J. Med. Chem., 47, pp. 4559-4569, 2004.

Lu et al., "Orphan Nuclear Receptors as eLiXiRs and FiXeRs of Sterol Metabolism", The Journal of Biological Chemistry, vol. 276, No. 41, pp. 37734-37738, Oct. 12, 2001.

Niesor et al., "The Nucelar Receptors FXR and LXRα: Potential Targets for the Development of Drugs Affecting Lipid Metabolism and Neoplastic Diseases" Current Pharmaceutical Design, No. 7, pp. 231-259, 2001.

Maloney et al., "Identification of a Chemical Tool for the Orphan Nuclear Receptor FXR", Journal of Medicinal Chemistry, vol. 43, No. 16, pp. 2971-2974, Aug. 10, 2000.

Hanley et al., "Fetal Epidermal Differentiation and Barrier Development In Vivo is Accelerated by Nuclear Hormone Receptor Activators", The Society for Investigative Dermatology, Inc., vol. 113, No. 5, pp. 788-795, Nov. 1999.

Niesor et al., "Synthetic Farnesoid X Receptor (FXR) Agonists: A New Class of Cholesterol Synthesis Inhibitors and Antiproliferative Drugs", Drugs of the Future, 24(4), pp. 431-438, 1999.

Hoffmann et al., "Interleukin-1 β-Induced Inhibition of Hair Growth In Vitro Is Mediated by Cyclic AMP", *The Journal of Investigative Dermatology*, vol. 108, pp. 40-42, 1997.

Hashizume et al., "Hair cycle-dependent expression of heat shock proteins in hair follicle epithelium", Int. J. of Dermatol., vol. 36, pp. 587-592, 1997.

Messenger, Andrew G., "The Control of Hair Growth: An Overview", *The Journal of Investigative Dermatology*, vol. 101, No. 1, pp. 4s-9s, 1993.

Weinberg et al., "Reconstitution of Hair Follicle Development In Vitro: Determination of Follicle Formation, Hair Growth, and Hair Quality by Dermal Cells", *The Journal of Investigative Dermatology*, vol. 100, pp. 229-236, 1993.

Ebling, F. John G., "The Biology of Hair", *Dermatologic Clinics*, vol. 5, No. 3, pp. 467-481, 1987.

Hattori et al., "Biochemical Analysis of Hair Growth From the Aspects of Aging and Enzyme Activities", *The Journal of Dermatology*, vol. 10, pp. 45-54, 1983.

Sato, Yoshio, "The Hair Cycle and Its Control Mechanism", pp. 3-13, 1976.

Adachi et al., "Human Hair Follicles: Metabolism and Control Mechanisms", *Journal of the Society of Cosmetic Chemists*, vol. 21, No. 13, pp. 901-924, 1970.

Narisawa et al., "Inhibitory Effects of Ursodeoxycholic Acid on N-Methyl-nitrosourea-Induced Colon Carcinogenesis and Colonic Mucosal Telomerase Activity in F344 Rats", J. Exp. Clin. Cancer Res., vol. 18, No. 2, pp. 259-266, 1999.

Katona et al., "Synethesis, Characterization, and Receptor Interaction in Profiles of Enantiomeric Bile Acids", J. Med. Chem., vol. 50, pp. 6048-6058, 2007.

Chen et al., Nuclear receptors, bile-acid detoxification, and cholestatis, www.thelancet.com, vol. 367, Feb. 11, 2006.

Pellicciari et al., 6α-Ethyl-Chenodeoxycholic Acid (6-ECDCA), a Potent and Selective FXR Agonist Endowed with Anticholestatic Activity, J. Med. Chem., vol. 45, No. 17, 2002.

* cited by examiner

REDUCTION OF HAIR GROWTH

BACKGROUND

The invention relates to reducing hair growth in mammals, particularly for cosmetic purposes.

A main function of mammalian hair is to provide environmental protection. However, that function has largely been lost in humans, in whom hair is kept or removed from various parts of the body essentially for cosmetic reasons. For example, it is generally preferred to have hair on the scalp but not on the face.

Various procedures have been employed to remove unwanted hair, including shaving, electrolysis, depilatory creams or lotions, waxing, plucking, and therapeutic antiandrogens. These conventional procedures generally have drawbacks associated with them. Shaving, for instance, can cause nicks and cuts, and can leave a perception of an increase in the rate of hair regrowth. Shaving also can leave an undesirable stubble. Electrolysis, on the other hand, can keep a treated area free of hair for prolonged periods of time, but can be expensive, painful, and sometimes leaves scarring. Depilatory creams, though very effective, typically are not recommended for frequent use due to their high irritancy potential. Waxing and plucking can cause pain, discomfort, and poor removal of short hair. Finally, antiandrogens—which have been used to treat female hirsutism—can have unwanted side effects.

It has previously been disclosed that the rate and character of hair growth can be altered by applying to the skin inhibitors of certain enzymes. These inhibitors include inhibitors of 5-alpha reductase, ornithine decarboxylase, S-adenosylmethionine decarboxylase, gamma-glutamyl transpeptidase, and transglutaminase. See, for example, Breuer et al., U.S. Pat. No. 4,885,289; Shander, U.S. Pat. No. 4,720,489; Ahluwalia, U.S. Pat. No. 5,095,007; Ahluwalia et al., U.S. Pat. No. 5,096,911; and Shander et al., U.S. Pat. No. 5,132,293.

Farnesoid X receptor (also known as "FXR", "RIP14", "bile acid receptor", "BAR", "HRR1" and "NR1H4") is a member of the family of ligand-activated transcription factors that bind to specific cis-acting regulatory elements in the promoters of their target genes and modulate gene expression in response to ligands. Some of these receptors bind to their target genes as dimers consisting of two molecules of the same receptor (homodimers), while others bind to as dimers consisting of one molecule each of two different receptors (heterodimers). Farnesoid X receptor forms a heterodimer with the retinoid X receptor (RXR) and binds to an inverted hexanucleotides repeat spaced by one nucleotide in the promoters of its target genes. Farnesoid X receptor is activated through interaction with ligands such as farnesoids and bile acids. In addition, coactivators (DRIP205/TRAP220, SRC-1 and PGC-1 alpha) that bridge between the ligand-activated farnesoid X receptors and the basal transcription machinery, and/or influence the chromatin structure, can enhance the transcriptional activity of farnesoid X receptor.

Farnesoid X receptor helps maintain bile acid homeostasis by modulating the expression of genes involved in the synthesis and transport of bile acid. Bile acids are the end product of cholesterol catabolism. Synthesis of bile acid is the predominant mechanisms for the excretion of excess cholesterol. Most bile acids in human are chenodeoxycholic acid, cholic acid, deoxycholic acid, ursodeoxycholic acid and lithocholic acid. While the level of bile acids is increased, farnesoid X receptor is activated and upregulates the expression of the bile salt export pump that is responsible for bile acid excretion. In addition to bile acid excretion, bile acid-activated farnesoid X receptor represses the transcription of cholesterol 7alpha-hydroxylase (CYP7A1), which the rate-limiting enzyme in the bile acid biosynthesis pathway.

SUMMARY

In one aspect, the invention provides a method (typically a cosmetic method) of reducing unwanted mammalian (preferably human) hair growth by applying to the skin an agonist of farnesoid X receptor in an amount effective to reduce hair growth. Preferably, the agonist interacts strongly with the farnesoid X receptor. The unwanted hair growth may be undesirable from a cosmetic standpoint.

In another aspect, the invention provides a method of reducing unwanted mammalian hair growth by applying to the skin a compound selected from the group consisting of bile acids, analogs of bile acids, and derivatives of bile acids.

In another aspect, the invention provides a method of reducing unwanted mammalian hair growth by applying to the skin a compound selected from the group consisting of farnesoids, analogs of farnesoids, and derivatives of farnesoids.

In a another aspect, the invention provides a method of reducing unwanted mammalian hair growth by applying to the skin a compound that increases the formation of FXR-RXR heterodimer, the expression of farnesoid X receptor, or promotes coactivator recruitment and interaction with FXR-RXR heterodimer.

In a further aspect, the invention provides a method of providing a benefit to exfoliated skin by applying any of the above agonists/compounds.

Typically, in practicing the aforementioned methods, the agonist/compound will be included in a topical composition along with a dermatologically or cosmetically acceptable vehicle. Accordingly, the present invention also relates to topical compositions comprising a dermatologically or cosmetically acceptable vehicle and an agonist of farnesoid X receptor. The present invention further relates to topical compositions comprising a dermatologically or cosmetically acceptable vehicle and (a) a compound selected from the group consisting of bile acids, analogs or derivatives of bile acids; (b) a compound selected from the group consisting of farnesoids, analogs or derivatives of farnesoids; and/or (c) a compound that increases the formation of FXR-RXR heterodimer, the expression of farnesoid X receptor, or promotes coactivator recruitment and interaction with FXR-RXR heterodimer.

In addition, the present invention relates to the use of an agonist of farnesoid X receptor for the manufacture of a therapeutic topical composition for reducing hair growth. Further, the present invention relates to the use of a compound for the manufacture of a therapeutic topical composition for reducing hair growth, wherein the compound is (a) a compound that selected from the group consisting of bile acids, analogs or derivatives of bile acids; (b) a compound selected from the group consisting of farnesoids, analogs or derivatives of farnesoids; and/or (c) a compound that increases the formation of FXR-RXR heterodimer, the expression of farnesoid X receptor, or promotes coactivator recruitment and interaction with FXR-RXR heterodimer.

In some embodiments, the agonist/compound is not a carbamate or ester of α-difluoromethylornithine. Carbamates, esters, and other conjugates of α-difluoromethylornithine are described in U.S. Ser. No. 10/397,132, which was filed on Mar. 26, 2003, is owned by the same owner as the present application, and is hereby incorporated herein by reference.

"Agonist of farnesoid X receptor", as used herein, means a compound that activates farnesoid X receptor.

An agonist that "interacts strongly" with the farnesoid X receptor is one that binds the receptor with such affinity that it elicits a response that is at least approximately comparable to (in magnitude) to that elicited by farnesoids.

Specific compounds include both the compound itself and pharmacologically acceptable salts of the compound.

Other features and advantages of the invention may be apparent from the detailed description and from the claims.

DETAILED DESCRIPTION

An example of a preferred composition includes at least one agonist of farnesoid X receptor in a cosmetically and/or dermatologically acceptable vehicle. The composition may be a solid, semi-solid, or liquid. The composition may be, for example, a cosmetic and dermatologic product in the form of an, for example, ointment, lotion, foam, cream, gel, or solution. The composition may also be in the form of a shaving preparation, an aftershave or an antiperspirant. The vehicle itself can be inert or it can possess cosmetic, physiological and/or pharmaceutical benefits of its own.

Examples of agonists of farnesoid X receptor include bile acids, farnesoids, their analogs and derivatives, and other compounds.

Derivatives and analogs of bile acids are known. For example, J. Med. Chem. (2004), 47, 4559-4569 describes bile acid derivatives. J. Biol. Chem. (2004), 279(10),8856-8861. describes various bile acids. Derivatives and analogs of farnesoids are known. For example, U.S. Pat. No. 6,187,814 describes farnesoid derivatives. Other examples of agonists of farnesoid X receptor are disclosed in WO200400752 1, WO3015771, WO2004048349, WO3076418, WO2004046162, WO3060078, WO2072598, WO3080803, WO2003086303, WO 2004046068, U.S. Pat. 20030187042, U.S. Pat. 0040176426, U.S. Pat. 20040180942, U.S. Pat. No. 6,452,032, U.S. Pat. 2003203939, U.S. Pat. 2005004165, J. med. Chem. (2000), 43(6), 2971-2974, Mol. Gen. Met. (2004), 83, 184-187, Drugs for the future 91999), 24(4), 431-438, Current Pharmaceutical Design (2001), 7, 231-259. Examples of coactivators involved in FXR-RXR hetrodimer are disclosed in Genes & Dev. (2004), 18, 157-169 and J. Biol. Chem. (2004), 279(35), 36184-36191. All of these references are incorporated by reference.

Specific examples of agonists of farnesoid X receptor are provided in Tables I.

TABLE I

Examples of Farnesoid X receptor agonists

Farnesol
Farnesal
Farnesyl acetate
Farnesoic acid
Methyl farnesyl ether
Methyl farnesoate
Ethyl farnesyl ether
Ethyl farnesoate
7-Methyl-9-(3,3-dimethyloxivanyl)-3-methyl-2,6-nonadienoic acid methyl ester (also known as Juvenile hormone III)
Lithocholic acid
Cholic acid
Deoxycholic acid
Chenodeoxycholic acid
Ursodeoxycholic acid
6-alpha-Ethyl chenodeoxycholic acid
Benzenesulfonamide, N-(2,2,2-trifluoroethyl)-N-[4-[2,2,2-trifluoro-1-hydroxy-1-(trifluoromethyl)ethyl]phenyl]-(also known as T0901317)

TABLE I-continued

Examples of Farnesoid X receptor agonists

Benzoic acid, 3-[2-[2-chloro-4-[[3-(2,6-dichlorophenyl)-5-(1-methylethyl)-4-isoxazolyl]methoxy]phenyl]ethenyl]- (also known as GW4064)
Phosphonic acid, [[3,5-bis(1,1-dimethylethyl)-4-hydroxyphenyl]ethenylidene]bis-, tetraethyl ester (also known as SR-12813)
Phosphonic acid, [2-[3,5-bis(1,1-dimethylethyl)-4-hydroxyphenyl]ethylidene]bis-, tetrakis(1-methylethyl) ester (also known as SR-45023A or apomine)
Phosphonic acid, [2-[3,5-bis(1,1-dimethylethyl)-4-hydroxyphenyl]ethylidene]bis-, tetraethyl ester (also known as SR-9213)
Phosphonic acid, [[3,5-bis(1,1-dimethylethyl)-4-hydroxyphenyl]ethenylidene]bis-, tetrakis(1-methylethyl) ester (also known as SR-12823i)
7-Methyl-9-(3,3-dimethyloxivanyl)-3-methyl-2,6-nonadienoic acid ethyl ester
3α,7α-dihydroxy-6α-ethyl-5p-cholan-24-oic acid
3α,7α-dihydroxy-6α-propyl-5p-cholan-24-oic acid
3α,7α-dihydroxy-6α-allyl-5p-cholan-24-oic acid The composition may include more than one agonist of farnesoid X receptor. In addition, the composition may include one or more other types of hair growth reducing agents, such as those described in U.S. Pat. Nos. 4,885,289; 4,720,489; 5,132,293; 5,096,911; 5,095,007; 5,143,925; 5,328,686; 5,440,090; 5,364,885; 5,411,991; 5,648,394; 5,468,476; 5,475,763; 5,554,608; 5,674,477; 5,728,736; 5,652,273; WO 94/27586; WO 94/27563; and WO 98/03149, all of which are incorporated herein by reference.

The concentration of the agonist in the composition may be varied over a wide range up to a saturated solution, preferably from 0.1% to 30% by weight or even more; the reduction of hair growth increases as the amount of agonist applied increases per unit area of skin. The maximum amount effectively applied is limited only by the rate at which the agonist penetrates the skin. The effective amounts may range, for example, from 10 to 3000 micrograms or more per square centimeter of skin.

The vehicle can be inert or can possess cosmetic, physiological and/or pharmaceutical benefits of its own. Vehicles can be formulated with liquid or solid emollients, solvents, thickeners, humectants and/or powders. Emollients include stearyl alcohol, mink oil, cetyl alcohol, oleyl alcohol, isopropyl laurate, polyethylene glycol, petroleum jelly, palmitic acid, oleic acid, and myristyl myristate. Solvents include ethyl alcohol, isopropanol, acetone, diethylene glycol, ethylene glycol, dimethyl sulfoxide, and dimethyl formamide.

The composition optionally can include components that enhance the penetration of the agonist into the skin and/or to the site of action. Examples of penetration enhancers include urea, polyoxyethylene ethers (e.g., Brij-30 and Laureth-4), 3-hydroxy-3,7,11-trimethyl-1,6,10-dodecatriene, terpenes, cis-fatty acids (e.g., oleic acid, palmitoleic acid), acetone, laurocapram, dimethylsulfoxide, 2-pyrrolidone, oleyl alcohol, glyceryl-3-stearate, propan-2-ol, myristic acid isopropyl ester, cholesterol, and propylene glycol. A penetration enhancer can be added, for example, at concentrations of 0.1% to 20% or 0.5% to 5% by weight.

The composition also can be formulated to provide a reservoir within or on the surface of the skin to provide for a continual slow release of the agonist. The composition also may be formulated to evaporate slowly from the skin, allowing the agonist extra time to penetrate the skin.

A topical cream composition containing an agonist of farnesoid X receptor may be prepared by mixing together water and all water soluble components in a mixing vessel-A.

The pH is adjusted in a desired range from about 3.5 to 8.0. In order to achieve complete dissolution of ingredients the vessel temperature may be raised to up to 45° C. The selection of pH and temperature will depend on the stability of the agonist. The oil soluble components, except for the preservative and fragrance components, are mixed together in another container (B) and heated to up to 70° C. to melt and mix the components. The heated contents of vessel B are poured into the water phase (container A) with brisk stirring. Mixing is continued for about 20 minutes. The preservative components are added at temperature of about 40° C. Stirring is continued until the temperature reaches about 25° C. to yield a soft cream with a viscosity of 8,000-12,000 cps, or a desired viscosity. The fragrance components are added at about 25° C.-30° C. while the contents are still being mixed and the viscosity has not yet built up to the desired range. If it is desired to increase the viscosity of the resulting emulsion, shear can be applied using a conventional homogenizer, for example a Silverson L4R homogenizer with a square hole high sheer screen. The topical composition can be fabricated by including the agonist in the water phase during formulation preparation or can be added after the formulation (vehicle) preparation has been completed. The agonist can also be added during any step of the vehicle preparation. The components of come cream formulations are described in the examples below.

EXAMPLE 1

Cream

| INCI Name | W/w (%) |
| --- | --- |
| DI Water | 61.00–75.00 |
| Agonist of farnesoid X receptor | 1.00–15.00 |
| Mineral oil | 1.90 |
| Glyceryl stearate | 3.60 |
| PEG 100 stearate | 3.48 |
| Cetearyl alcohol | 2.59 |
| Ceteareth-20 | 2.13 |
| Dimethicone, 100 ct | 0.48 |
| Lipidure PMB[a] | 3.00 |
| Advanced moisture complex[b] | 5.00 |
| Stearyl alcohol | 1.42 |
| Preservative, fragrance and color pigment | qs |
| Total | 100.00 |

[a]polyquartinium-51 (Collaborative Labs, NY);
[b]glycerin and water and sodium PCA and urea and trehalose and polyqauternium-51 and sodium hyaluronate (Collaborative Labs, NY)

EXAMPLE 2

Cream

| INCI Name | w/w (%) |
| --- | --- |
| Agonist of farnesoid X receptor | 0.5–15.00 |
| Glycerol (glycerin) | 0–5 |
| Isoceteth-20 | 3–7 |
| Glyceryl isostearate | 1.5–5 |
| Dicaprylyl ether | 3–15 |
| Glyceryl triacetate (triacetin) | 0.5–10 |
| Preservative, fragrance and color pigment | q.s. |
| Water | q.s. to 100.00 |

EXAMPLE 3

Cream

| INCI Name | w/w (%) |
| --- | --- |
| Agonist of farnesoid X receptor | 0.5–15.00 |
| Glycerol (glycerin) | 0–5 |
| Isoceteth-20 | 3–7 |
| Glyceryl isostearate | 1.5–5 |
| Dicaprylyl ether | 3–15 |
| 1-dodecyl-2-pyrrolidanone | 0.5–10% |
| Preservative, fragrance and color | q.s. |
| Water | to 100.00 |

EXAMPLE 4

Cream

| INCI Name | w/w (%) |
| --- | --- |
| Water | 70 |
| Glyceryl stearate | 4 |
| PEG-100 | 4 |
| Cetearyl alcohol | 3 |
| Ceteareth-20 | 2.5 |
| Mineral oil | 2 |
| Stearyl alcohol | 2 |
| Dimethicone | 0.5 |
| Preservatives | 0.43 |
| 1-Dodecyl-2-pyrrolidanone | 1–10 |
| Total | 100.00 |

An agonist of farnesoid X receptor is added to the example 4 formulation and mixed until solubilized.

EXAMPLE 5

Cream

| INCI Name | w/w (%) |
| --- | --- |
| Water | 70–80 |
| Glyceryl stearate | 4 |
| PEG-100 | 4 |
| Cetearyl alcohol | 3 |
| Ceteareth-20 | 2.5 |
| Mineral oil | 2 |
| Stearyl alcohol | 2 |
| Dimethicone | 0.5 |
| Preservatives | 0.43 |
| Monocaprylate/Caprate (Estol 3601, Uniquema, NJ) | 1–10 |
| Total | 100.00 |

An agonist of farnesoid X receptor is added to the example 5 formulation and mixed until solubilized.

EXAMPLE 6

Cream

| INCI Name | w/w (%) |
|---|---|
| Water | 70–80 |
| Glyceryl stearate | 4 |
| PEG-100 | 4 |
| Cetearyl alcohol | 3 |
| Ceteareth-20 | 2.5 |
| Mineral oil | 2 |
| Stearyl alcohol | 2 |
| Dimethicone | 0.5 |
| Preservatives | 0.43 |
| cis Fatty acids | 1–10 |
| Total | 100.00 |

An agonist of farnesoid X receptor is added to the example 6 formulation and mixed until solubilized.

EXAMPLE 7

Cream

| INCI Name | w/w (%) |
|---|---|
| Water | 70–80% |
| Glyceryl stearate | 4 |
| PEG-100 | 4 |
| Cetearyl alcohol | 3 |
| Ceteareth-20 | 2.5 |
| Mineral oil | 2 |
| Stearyl alcohol | 2 |
| Dimethicone | 0.5 |
| Preservatives | 0.43 |
| Terpene(s) | 1–10 |
| Total | 100.00 |

An agonist of farnesoid X receptor is added to the example 7 formulation and mixed until solubilized.

EXAMPLE 8

Cream

| INCI Name | w/w (%) |
|---|---|
| Water | 70–80% |
| Glyceryl stearate | 4 |
| PEG-100 | 4 |
| Cetearyl alcohol | 3 |
| Ceteareth-20 | 2.5 |
| Mineral oil | 2 |
| Stearyl alcohol | 2 |
| Dimethicone | 0.5 |
| Preservatives | 0.43 |
| Polyoxyethylene sorbitans (tween) | 1–10 |
| Total | 100.00 |

An agonist of farnesoid X receptor is added to the example 8 formulation and mixed until solubilized.

A hydroalcoholic formulation containing an agonist of farnesoid X receptor is prepared by mixing the formulation components in a mixing vessel. The pH of the formulation is adjusted to a desired value in the range of 3.5-8.0. The pH adjustment can also be made to cause complete dissolution of the formulation ingredients. In addition, heating can be applied to up to 45° C., or even up to 70° C. depending on the stability of the agonist to achieve dissolution of the formulation ingredients. The components of two hydroalcoholic formulations are listed below.

EXAMPLE 9

Hydro-Alcoholic

| INCI Name | w/w (%) |
|---|---|
| Water | 48.00–62.50 |
| An agonist of farnesoid X receptor | 0.5–15.00 |
| Ethanol | 16.00 |
| Propylene glycol | 5.00 |
| Dipropylene glycol | 5.00 |
| Benzyl alcohol | 400 |
| Propylene carbonate | 2.00 |
| Captex-300[a] | 5.00 |
| Total | 100.00 |

[a] caprylic/capric triglyceride (Abitec Corp., OH).

EXAMPLE 10

Hydro-Alcoholic

| INCI Name | w/w (%) |
|---|---|
| Water | 53.00–67.9 |
| An agonist of farnesoid X receptor | 0.1–15.00 |
| Ethanol | 16.00 |
| Propylene glycol | 5.00 |
| Dipropylene glycol dimethyl ether | 5.00 |
| Benzyl alcohol | 4.00 |
| Propylene carbonate | 2.00 |
| Total | 100.00 |

| INCI Name | w/w (%) |
|---|---|
| Ethanol (alcohol) | 80 |
| Water | 17.5 |
| Propylene glycol dipelargonate | 2.0 |
| Propylene glycol | 0.5 |
| Total | 100.00 |

EXAMPLE 11

Hydro-Alcoholic

An agonist of farnesoid X receptor is added to the example 11 formulation and mixed until solubilized.

The composition should be applied topically to a selected area of the body from which it is desired to reduce hair growth. For example, the composition can be applied to the face, particularly to the beard area of the face, i.e., the cheek, neck, upper lip, and chin. The composition also may be used as an adjunct to other methods of hair removal including shaving, waxing, mechanical epilation, chemical depilation, electrolysis and laser-assisted hair removal. Other actions that make their concept appearance are concurrent skin benefits in addition to hair reduction.

The composition can also be applied to the legs, arms, torso or armpits. The composition is suitable, for example, for reducing the growth of unwanted hair in women. In humans, the composition should be applied once or twice a day, or even more frequently, to achieve a perceived reduction in hair growth. Perception of reduced hair growth could occur as early as 24 hours or 48 hours (for instance, between normal shaving intervals) following use or could take up to, for example, three months. Reduction in hair growth is demonstrated when, for example, the rate of hair growth is slowed, the need for removal is reduced, the subject perceives less hair on the treated site, or quantitatively, when the weight of hair removed (i.e., hair mass) is reduced.

Human Hair Follicle Growth Assay:

Human hair follicles in growth phase (anagen) were isolated from face-lift tissue (obtained from plastic surgeons) under dissecting scope using a scalpel and watchmakers forceps. The skin was sliced into thin strips exposing 2-3 rows of follicles that could readily be dissected. Follicles were placed into 0.5 ml William's E medium (Life Technologies, Gaithersburg, Md.) supplemented with 2 mM L-glutamine, 10 µg/ml insulin, 10 ng/ml hydrocortisone, 100 units of penicillin, 0.1 mg/ml streptomycin and 0.25 µg/ml amphotericin B. The follicles were incubated in 24-well plates (1 follicle/well) at 37° C. in an atmosphere of 5% $CO_2$ and 95% air. Compounds are dissolved into dimethyl sulfoxide as 100-fold stock solution. The control hair follicles were treated with dimethyl sulfoxide without prostaglandin. The follicles were photographed in the 24-well plates under the dissecting scope at a power of 10×. Typically, image recordings were made on day 0 (day follicles were placed in culture), and again on day 7. The length of hair follicle was assessed using an image analysis software system. The growth of hair fiber was calculated by the subtracting the follicle length on day 0 from that determined on day 7.

Hamster Hair Mass Assay:

Hamster hair mass was determined using a method similar to that described in previous patent (US2004/0198821).

The agonists of farnesoid X receptor demonstrated a significant reduction of human hair follicle growth. All of the six agonists of farnesoid X receptor tested significantly reduced hair growth. The results are provided in Table II. The hair growth inhibition profile by the agonists of farnesoid X receptor was found to be dose-dependent. The results are provided in Table III.

TABLE II

Inhibition of human hair follicle growth by the agonists of farnestoid X receptor.

| FXR agonists | Dose (µM) | Hair follicle length increase (mm) | | |
|---|---|---|---|---|
| | | Treated | Control | % Inhibition |
| Deoxycholic acid | 100 | 0.06 ± 0.05 | 1.07 ± 0.14 | 94.3 ± 4.7 |
| Ursodeoxycholic acid | 200 | 0.20 ± 0.11 | 1.07 ± 0.14 | 81.3 ± 10.3 |
| Chenodeoxycholic acid | 100 | 0.05 ± 0.06 | 1.07 ± 0.14 | 95.3 ± 5.6 |
| Lithocholic acid | 50 | 0.02 ± 0.02 | 1.07 ± 0.14 | 98.1 ± 1.9 |
| Farnesol | 100 | 0.04 ± 0.07 | 0.87 ± 0.23 | 95.4 ± 8.0 |
| Juvenile hormone III | 100 | 0.21 ± 0.15 | 0.87 ± 0.23 | 75.9 ± 17.2 |

TABLE III

Dose-dependent reduction of human hair follicle growth by the agonists of farnestoid X receptor.

| FXR agonists | Dose (µM) | Growth of follicle (mm) | | |
|---|---|---|---|---|
| | | Treated | Control | % Reduction |
| Deoxycholic acid | 10 | 1.20 ± 0.49 | 1.76 ± 0.36 | 31.8 ± 18.1 |
| | 50 | 0.54 ± 0.34 | 1.76 ± 0.36 | 69.3 ± 13.6 |
| | 100 | 0.54 ± 0.34 | 1.76 ± 0.36 | 69.3 ± 13.6 |
| Ursodeoxycholic acid | 50 | 1.12 ± 0.24 | 1.76 ± 0.36 | 36.3 ± 13.6 |
| | 100 | 0.86 ± 0.20 | 1.76 ± 0.36 | 51.1 ± 11.4 |
| | 150 | 0.61 ± 0.20 | 1.76 ± 0.36 | 65.3 ± 11.4 |
| Chenodeoxycholic acid | 5 | 1.53 ± 0.29 | 1.55 ± 0.02 | 1.3 ± 18.7 |
| | 25 | 0.79 ± 0.27 | 1.55 ± 0.02 | 49.0 ± 17.4 |
| | 50 | 0.13 ± 0.10 | 1.55 ± 0.02 | 91.6 ± 6.5 |
| Lithocholic acid | 2 | 0.82 ± 0.14 | 1.24 ± 0.23 | 33.9 ± 11.3 |
| | 10 | 0.44 ± 0.16 | 1.24 ± 0.23 | 64.5 ± 12.9 |
| | 20 | 0.03 ± 0.06 | 1.24 ± 0.23 | 97.6 ± 4.8 |

Furthermore, the agonists of farnestoid X receptor were tested in the hamster hair mass assay. The agonists reduced hair mass in vivo as shown in Table IV.

TABLE IV

Reduction of hamster hair mass by the agonists of farnestoid X receptor.

| FXR agonists | Dose (w/v) | Vehicle* | Hair mass (mg) | | |
|---|---|---|---|---|---|
| | | | Treated | Control | % Inhibition |
| Lithocholic acid | 4% | ethanol | 1.01 ± 0.12 | 1.96 ± 0.19 | 46.4 ± 6.0 |
| Chenodeoxycholic acid | 5% | ethanol | 0.54 ± 0.08 | 2.28 ± 0.19 | 76.4 ± 2.6 |
| Deoxycholic acid | 5% | ethanol | 0.92 ± 0.14 | 2.66 ± 0.28 | 63.6 ± 6.0 |
| Ursodeoxycholic acid | 5% | ethanol | 1.02 ± 0.16 | 2.43 ± 0.31 | 56.8 ± 3.8 |

*The vehicle contains 90% ethanol and 10% propylene glycol.

Accordingly, other embodiments are within the scope of the following claims.

What is claimed is:

1. A method of reducing mammalian hair growth which comprises
   selecting an area of skin from which reduced hair growth is desired; and
   applying to said area of skin a dermatologically acceptable composition comprising a bile acid in an amount effective to reduce hair growth,
   wherein said bile acid is not ursodeoxycholic acid or chenodeoxycholic acid.

2. The method of claim 1, wherein said bile acid is lithocholic acid.

3. The method of claim 1, wherein said bile acid is deoxycholic acid.

4. The method of claim 1, wherein the concentration of said bile acid in said composition is between 0.1% and 30%.

5. The method of claim 1, wherein the composition provides a reduction in hair growth of at least 30% when tested in the Human Hair Follicle assay.

6. The method of claim 1, wherein said hair growth comprises androgen stimulated hair growth.

7. The method of claim 1, wherein the composition further includes a second component that also causes a reduction in hair growth.

8. The method of claim 1, wherein said bile acid is cholic acid.

9. The method of claim 1, wherein said bile acid is $3\alpha, 7\alpha$-dihydroxy-$6\alpha$-ethyl-5p-cholan-24-oic acid.

10. The method of claim 1, wherein said bile acid is $3\alpha, 7\alpha$-dihydroxy-$6\alpha$-propyl-5p-cholan-24-oic acid.

11. The method of claim 1, wherein said bile acid is $3\alpha, 7\alpha$-dihydroxy-$6\alpha$-allyl-5p-cholan-24-oic acid.

* * * * *

UNITED STATES PATENT AND TRADEMARK OFFICE
CERTIFICATE OF CORRECTION

PATENT NO. : 7,618,956 B2
APPLICATION NO. : 11/141798
DATED : November 17, 2009
INVENTOR(S) : Cheng Shine Hwang Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 984 days.

Signed and Sealed this

Twenty-sixth Day of October, 2010

David J. Kappos
*Director of the United States Patent and Trademark Office*